(12) United States Patent
Campbell et al.

(10) Patent No.: US 8,909,660 B2
(45) Date of Patent: Dec. 9, 2014

(54) SYSTEM AND METHOD FOR SECURED HEALTH RECORD ACCOUNT REGISTRATION

(75) Inventors: Janet L. Campbell, Madison, WI (US); Dustin L. Gage, Madison, WI (US); Erv Walter, Sun Prairie, WI (US); Carl Dvorak, Verona, WI (US)

(73) Assignee: Epic Systems Corporation, Verona, WI (US)

( * ) Notice: Subject to any disclaimer, the term of this patent is extended or adjusted under 35 U.S.C. 154(b) by 508 days.

(21) Appl. No.: 13/267,483

(22) Filed: Oct. 6, 2011

(65) Prior Publication Data

US 2012/0072237 A1 Mar. 22, 2012

Related U.S. Application Data

(63) Continuation-in-part of application No. 12/753,241, filed on Apr. 2, 2010.

(60) Provisional application No. 61/390,912, filed on Oct. 7, 2010, provisional application No. 61/166,596, filed on Apr. 3, 2009.

(51) Int. Cl.
| | |
|---|---|
| G06F 17/30 | (2006.01) |
| G06F 7/00 | (2006.01) |
| G06Q 50/24 | (2012.01) |
| G06F 21/62 | (2013.01) |
| G06Q 50/22 | (2012.01) |
| G06F 19/00 | (2011.01) |

(52) U.S. Cl.
CPC ............... *G06Q 50/22* (2013.01); *G06Q 50/24* (2013.01); *G06F 19/323* (2013.01); *G06F 19/322* (2013.01); *G06F 21/6245* (2013.01); *G06F 2221/2153* (2013.01)
USPC ......................................... 707/758; 707/743

(58) Field of Classification Search
CPC .... G06F 19/328; G06F 19/323; G06F 19/327
USPC ............................................ 707/758; 715/743
See application file for complete search history.

(56) References Cited

U.S. PATENT DOCUMENTS

| | | | | |
|---|---|---|---|---|
| 6,264,614 | B1 * | 7/2001 | Albert et al. ................... | 600/528 |
| 6,751,730 | B1 * | 6/2004 | Walker et al. ................. | 713/161 |
| 6,988,075 | B1 * | 1/2006 | Hacker ............... | 705/3 |
| 7,143,437 | B2 * | 11/2006 | Royer et al. ...................... | 726/8 |
| 7,209,886 | B2 * | 4/2007 | Kimmel ........................... | 705/3 |
| 7,225,408 | B2 * | 5/2007 | O'Rourke ...................... | 715/743 |
| 7,275,156 | B2 * | 9/2007 | Balfanz et al. ................ | 713/168 |
| 7,289,988 | B2 * | 10/2007 | Joseph ................... | 707/999.006 |
| 7,555,720 | B2 * | 6/2009 | O'Rourke ...................... | 715/739 |

(Continued)

*Primary Examiner* — Pavan Mamillapalli
(74) *Attorney, Agent, or Firm* — Boyle Fredrickson, S.C.

(57) ABSTRACT

A computer-implemented system is used for implementing an improved personal health record enrollment process. The system includes an electronic medical record system configured to generate configured to generate an index file, the index file associated with patient medical data including the clinical records of the patient, wherein the index file is augmented with encrypted metadata generated based on the patient medical data and configured to include patient authentication information. The system further includes a personal health record web portal configured to implement a patient enrollment process including the steps of receiving patient authentication input, authenticating the patient authentication input based on the received patient authentication input and the encrypted metadata in the index file, and generating a patient enrollment account for the patient based at least in part on the patient authentication information.

22 Claims, 8 Drawing Sheets

(56) References Cited

U.S. PATENT DOCUMENTS

| | | |
|---|---|---|
| 7,661,146 B2 * | 2/2010 | Karimzadeh et al. .......... 726/27 |
| 7,685,001 B2 * | 3/2010 | Haider et al. .................. 705/2 |
| 8,498,884 B2 * | 7/2013 | Maitland et al. ................ 705/3 |
| 2002/0158911 A1 * | 10/2002 | O'Rourke .................. 345/810 |
| 2004/0143454 A1 * | 7/2004 | Kimmel ........................ 705/2 |

* cited by examiner

SYSTEM AND METHOD FOR SECURED HEALTH RECORD ACCOUNT REGISTRATION

CROSS REFERENCE TO RELATED APPLICATIONS

This application claims the benefit of U.S. Provisional Application 61/390,912, filed Oct. 7, 2010. This application is further a continuation in part of U.S. patent application Ser. No. 12/753,241, filed Apr. 2, 2010, which further claims the benefit of U.S. Provisional Application No. 61/166,596, filed Apr. 3, 2009, all of which are hereby incorporated by reference.

BACKGROUND OF THE INVENTION

The present invention relates to electronic medical records and, in particular, to a system and method for improving a personal health record enrollment process using electronic medical records stored on removable media.

Personal health record (PHR) websites allow a patient to record patient-sourced health data and provide general health-related information. A patient may use a PHR site, for example, to keep a healthcare diary, record medications, track information such as weight or blood pressure, etc. These personal health record sites serve a valuable purpose in creating and preserving patient-sourced data. Personal health record websites are typically stand alone systems containing records uploaded by a user. However, a personal health record may be provided within a portal associated with a hospital or other care facility containing records maintained by healthcare professionals.

These sites may also provide continuity in a patient's medical information recordkeeping when healthcare providers are changed or multiple healthcare providers are used. Some personal health record sites allow data to be uploaded, transferred, and/or copied from electronic portals of healthcare institutions. Documents may be stored using a common format, such as the Cross-Enterprise Document Media Interchange (XDM), which provide document interchange using common file and directory structure over several standard media. This permits a user to use physical media to carry medical documents. Although these sites allow a patient to receive and carry localized data, the data contained therein may quickly become outdated and this provide users with the ability to view or download those records.

Other personal health record sites are provided as an integral part of the medical record system of the healthcare institution, acting as a portal to the information contained in that system. This inclusion of the medical record system data means that the PHR site may serve as a localized health record repository for the patient. One example of such a system is the MyChart PHR system provided by the Epic Systems Corporation of Verona, Wis. and described in United States Patent Application 20030208381 filed Mar. 29, 2001 and entitled: Patient Health Record Access System, incorporated herein by reference.

When a patient chooses to upload his medical information to either an unconnected-PHR or a portal PHR that is not affiliated with the organization or entity that authored the medical information, the process greatly facilitated by emerging standards for electronic medical records which define standard formats for such data. Standardized formats allow the data to be readily integrated into the familiar environment of the PHR. Generally, such standards are designed to promote continuity in a patient's healthcare records as the patient moves among healthcare providers over the course of his or her life. Ideally, a universal standard or set of translatable standards allows patients to easily transfer their electronic medical files to a new healthcare provider, for example over the Internet, as the patients change healthcare providers.

Current standards for electronic medical records anticipate that some data transfers will employ removable storage media such as optical disks or flash memory drives (thumb drives) receiving downloaded electronic medical records that are then physically transported by the patient. The downloaded files, formatted for storage on such media, may include a human readable index file to assist the end user in identifying the files and uploading them to an electronic medical record system at a receiving institution. This index file can be formatted, for example in HTML, for viewing on a standard browser.

BRIEF SUMMARY OF THE INVENTION

The present inventors have recognized that health record files stored in removable media can be simply augmented to include encrypted patient identification information that will allow the patient to register and upload the health record files to one personal health record website without requiring that the patient separately register with the PHR website and initiate communication with the healthcare provider that originated the health record files. The PHR website of the system described herein does not require prearranged secure communication with the healthcare organization including the type of business associate agreement and protections that may be required for a more tightly integrated relationship. The downloaded data may carry with it encrypted information including an authentication mechanism of the user identification.

According to one exemplary embodiment, a computer-implemented system is used for implementing an improved personal health record enrollment process. The system includes an electronic medical record system configured to generate a downloaded, or otherwise provided, index file in a format viewable in a browser interpreting HTML, the index file including patient medical data including the clinical records of the patient accessible by at least one HTML link, wherein the downloaded index file is augmented with encrypted metadata generated based on the patient medical data and configured to provide patient authentication information. This record package is designed for patients who wish to make their medical information portable, either by downloading the record themselves from a web portal or portal PHR provided by the authoring healthcare organization, or by receiving the record package on portable media from the authoring healthcare organization. The system further includes a personal health record website, unconnected to the original authoring organization, configured to implement a patient enrollment process including the steps of decrypting the encrypted metadata to receive patient authentication information, generating a patient enrollment account for the patient based on the patient authentication information, and receiving the patient medical data for storage and association with the patient enrollment account.

DETAILED DESCRIPTION OF THE PREFERRED EMBODIMENT

Figure 1:
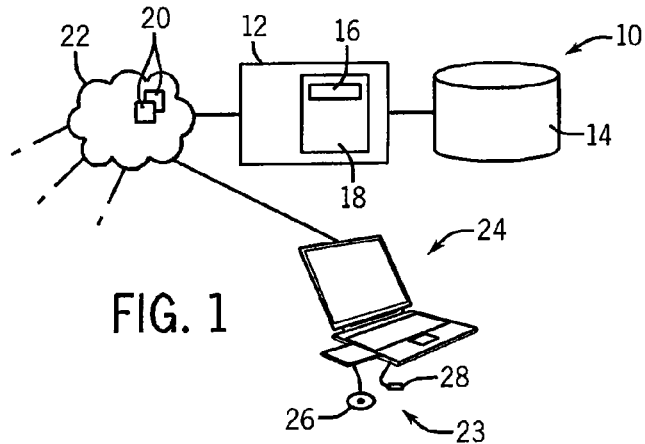
FIG. 1 is a diagram showing the interconnection of a personal health record (PHR) server computer and patient client computers to implement a PHR website.

Referring now to FIG. 1, a personal health record (PHR) website system 10 may include an electronic computer 12 of the type well known in the art communicating with a mass storage device 14 such as a disk drive array to implement a database linked to a Web server according to a stored PHR program 16 stored in an electronic memory 18 of computer 12. PHR website system 10 is a standalone system that is not integrated in, for example, an electronic medical record system of a healthcare institution.

PHR website system 10 may be configured to serve a set of web pages 20 on the Internet 22 providing a display of information to patients, including, for example, medical data entered by the patient and stored on the mass storage device 14, uploaded clinical medical data, and links to informative medical articles. The web pages 20 may also provide tools for monitoring and displaying patient health programs and activities, as well as providing portal connections to healthcare institutions permitting, for example, the patient to make appointments, track lab test results, query physicians, and receive notifications for activities and/or informational articles relevant to the patient sponsored by the healthcare institution.

A PHR website system 10 may be implemented as a standalone system. In comparison, a PHR portal system may be implemented in connection with a medical record or other system associated with a healthcare institution. Association with a specific institution may facilitate incorporation of data in the PHR portal system while the PHR website generally requires the user to manage the associated data.

Connection with the PHR website system 10 is provided by a standard browser program (not shown), for example, executing on a personal computer 24 under control of the patient that is connected with the Internet 22 to receive the web pages 20. The personal computer 24 may accept removable media 23, such as CD-ROM 26 or USB memory sticks 28 or the like, for reading from and writing to such removable media 23.

Computer 24 may be configured to use the removable media 23 to store portable medical records from a PHR database of a previous medical record system, stored on mass storage device 14 and including clinical medical records and patient-sourced medical data. The portable medical records may be stored in any of a variety of different forms including a Continuity of Care Document (CCD), being an XML-based markup standard specifying a standard for the encoding, structure and semantics of medical information. The standard requires that the stored records include a human-readable textual portion, which allows interpretation of the records without the benefit of their inclusion in a medical record or other system, and one or more structured portions for software processing by medical record systems that will allow the records to be easily uploaded to a new medical record system. The human-readable textual portion contains a textual version of a patient's medical record including administrative, demographic, and clinical information facts about a patient's healthcare covering one or more healthcare encounters from a medical provider, the patient-sourced medical data, etc.

The Continuity of Care Document provides a means for one healthcare practitioner, system, or setting to aggregate all of the pertinent data about a patient and forward it to another practitioner, system, or setting to support the continuity of care. Its primary use case is to provide a snapshot in time containing the pertinent clinical, demographic, and administrative data for a specific patient. In a continuity of care document, the human-readable textual portion is combined with the structured portion in a single XML-based document.

As is generally understood in the art, XML provides for text tags that demarcate types of content within a text data file. The resulting XML file is generally human readable but designed to be machine interpretable and thus is difficult for many patients to understand. The computer 24 may upload medical data from the removable media 23 to the PHR website 10 and conversely may also be used to receive downloaded data from that PHR website 10.

Figure 2A:
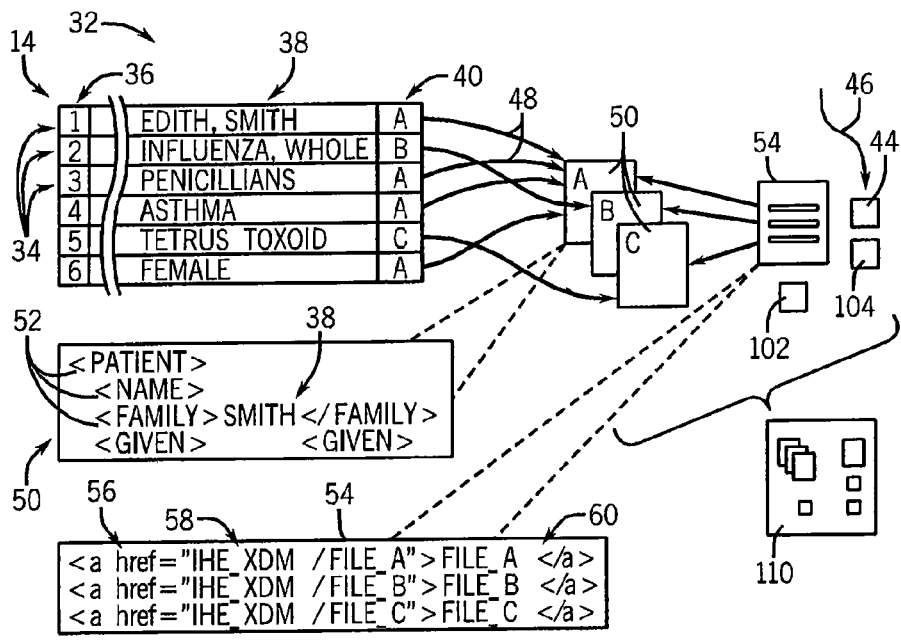
FIG. 2A is a data flow diagram showing extraction of data from medical records held by the PHR into downloadable medical data files and an index file.
Figure 4:
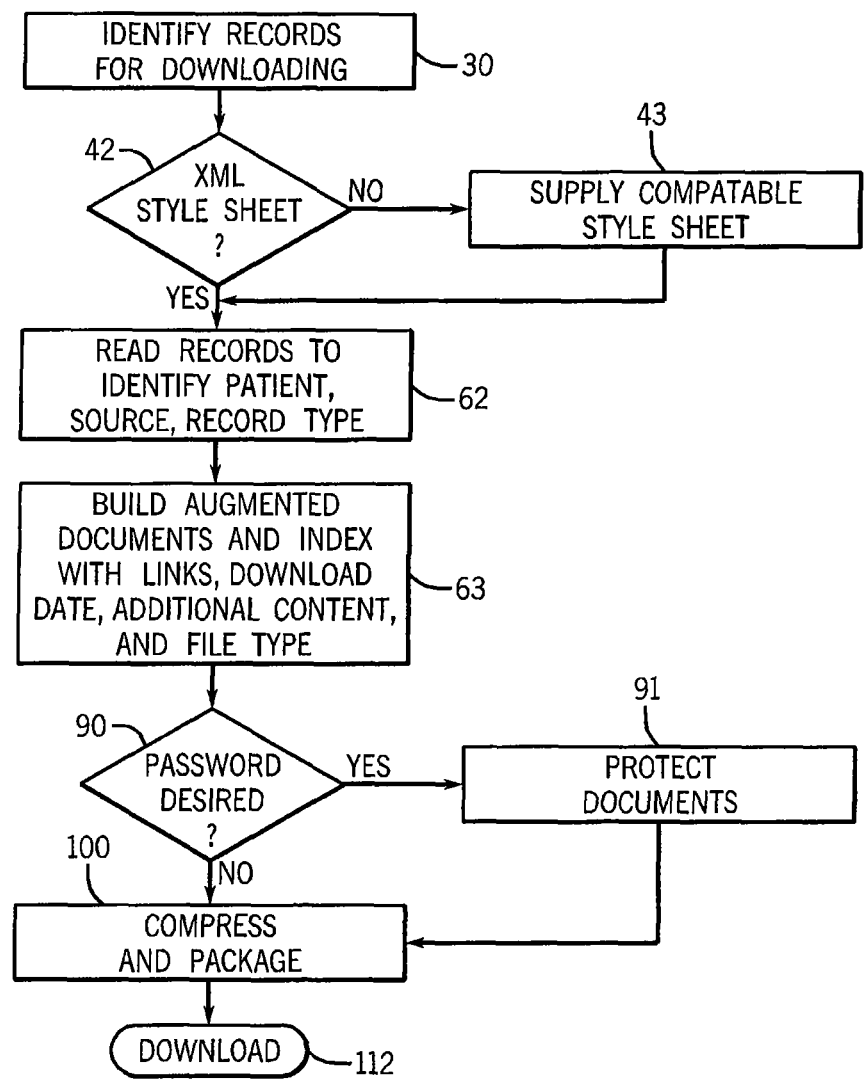
FIG. 4 is a flow chart of the steps executed by the PHR server computer of FIG. 1 to implement the augmentation of FIG. 3.

Referring now to FIGS. 2 and 4, in this latter situation, commands from the browser executing on the computer 24 (and sent to computer 12) may be used to initiate a downloading of medical data from the PHR database, shown as database 32 in FIG. 2A, per process block 30. This downloading process is normally preceded by authentication steps in which the patient provides a user name and password and logs onto the PHR website 10 to obtain access to medical data associated with the patient or persons related to or under the care of the patient. The computer 12 executing the PHR program 16 may then provide a list of downloadable medical data files to the patient allowing him or her to select particular files for downloading.

These files available for downloading may be files that were previously uploaded in a standard format (such as CCD) or that are newly created based on healthcare encounters from a healthcare institution and held as such or incorporated into the database, may be data sourced by the patient him or herself and incorporated into the database 32, may be data uploaded from healthcare provided by other healthcare institutions, etc.

Generally the database 32 will comprise a set of records 34 each having a unique record identifier 36, a field indicating a type of medical data of the record (not shown), the value of the medical data 38 of the records, and the data source 40 of the medical data 38 (e.g., a hospital or clinic name or the patient). In this example, the data source may be the patient (A) or different medical institutions (B) and (C).

Types of medical data may include allergies, current medications, medical conditions, immunization history, care history, care providers, health concerns and the like.

For example, in selecting the particular files to be downloaded, the patient may opt to download medical data 38 from each of the sources (A-C). Alternative data selection techniques are also contemplated; for example, selecting medical data by date range or medical data type or the like. The selected data 38 may be taken from the integrated database 32 or, alternatively or in addition, from previously uploaded files maintained separately, for example, as original CCD documents.

The selected records 34, as indicated by arrows 48, may then be interpreted into a standard format for downloading, for example as CCD documents. In this process, the data 38 is organized and tagged with XML tags according to the CCD standard and incorporated into one or more downloadable medical data files 50. Generally, PHR program 16 may be configured to create medical data files 50 using text string medical data 38 from the records 34 and flanking this text with the appropriate XML tags 52 derived from the type of medical data recorded in the record 34. Examples may include allergies, current medications, medical conditions, immunization history, care providers, health concerns and the like. For example, an allergy stored in the system as "Allergy 35" might be expanded in XML to:

```
<entry>
    <act classCode="ACT" moodCode="EVN">
        <templateId root="2.16.840.1.113883.10.20.1.27"/>
        <templateId root="1.3.6.1.4.1.19376.1.5.3.1.4.5.1"/>
        <templateId root="1.3.6.1.4.1.19376.1.5.3.1.4.5.3"/>
        <templateId root="2.16.840.1.113883.3.88.11.32.6"/>
        <id extension="52" root="1.2.840.114350.1.13.123.1.7.2.768076"/>
        <code nullFlavor="NA"/>
        <statusCode code="active"/>
        <effectiveTime>
            <low value="20000101"/>
        </effectiveTime>
        <entryRelationship inversionInd="false" typeCode="SUBJ">
            <observation classCode="OBS" moodCode="EVN"
negationInd="false">
                <templateId root="1.3.6.1.4.1.19376.1.5.3.1.4.5"/>
                <templateId root="1.3.6.1.4.1.19376.1.5.3.1.4.6"/>
                <templateId root="2.16.840.1.113883.10.20.1.28"/>
                <templateId root="2.16.840.1.113883.10.20.1.18"/>
                <templateId extension="allergy" root="1.3.6.1.4.1.19376.1.5.3.1"/>
                <id extension="52" root="1.2.840.114350.1.13.123.1.7.2.768076"/>
                <code code="ALG" codeSystem="2.16.840.1.113883.5.4"
                    codeSystemName="ObservationIntoleranceType"
                    displayName="Allergy">
                    <originalText>
                        <reference value="#ALG1NAM"/>
                    </originalText>
                </code>
                <statusCode code="completed"/>
                <effectiveTime>
                    <low value="20000101/>
                    <high nullFlavor="PINF"/>
```

Alternatively, where the original uploaded CCD documents are preserved, those documents may be used as at least some of the medical data files 50. Generally multiple medical data files 50 may be created logically related to the request or the data organization at the PHR website 10. According to an exemplary embodiment, each file may be associated with a unique source of data.

Figure 2B:
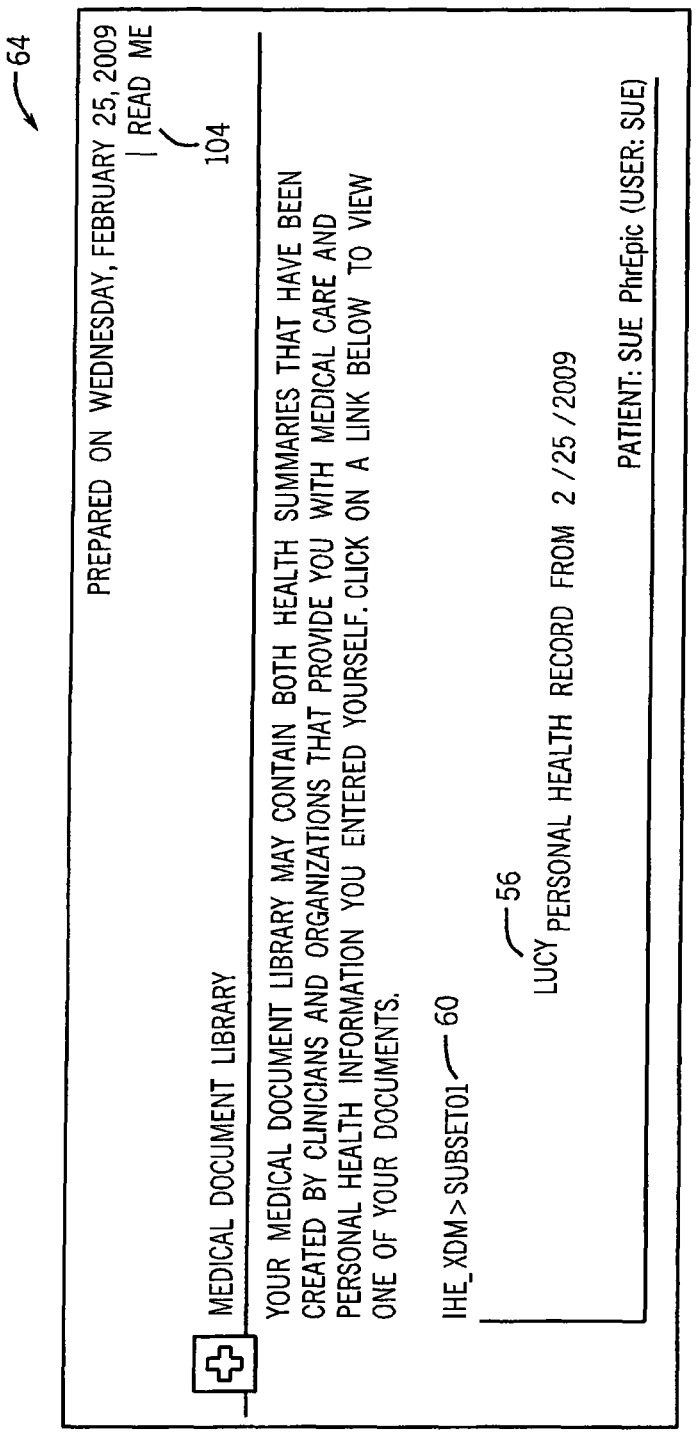
FIG. 2B is an exemplary index file created in the data flow of FIG. 2A.

Once the medical data files 50 have been populated with the desired information, an index file 54 is created. The index file 54 is an HTML file providing an HTML link 56 holding an index-relative address 58 for each of the medical data files 50 and a machine generated filename 60. Referring now to FIG. 2B, an exemplary index file 54 including an HTML link 56 labeled "Lucy" is shown. The index file 54 is designed to be opened in a browser and to direct a user to the particular medical data files 50 using standard browser operations (e.g., clicking on the hyperlinks 56) to permit viewing of the different medical files 50. Typically, the browser will render the data of the files 50 as unformatted text showing the XML tags and the medical data 38 as depicted in FIG. 2A.

The above-described initial stages of this process may, for example, conform to the teachings of the IHE ITI (Integrating the Healthcare Enterprise) technical framework revision 5.0, hereby incorporated by reference. This standard describes the format and file types, including the index file 54 and a ReadMe file 104, describing the source of the download for removable media 23.

The present inventors have recognized that the choice of encoding mechanisms (HTML, XML), which provide machine readability and file verification using any standard browser, creates the possibility of augmenting these files, in particular the index, to leverage the other capabilities of the browser in making this data readily accessible to the patient outside of the PHR website structure.

Referring still to FIGS. 2A and 4, the present invention first evaluates the medical data files 50 to associate one or more of the files 50 with an XML stylesheet 44 matched to the file type (e.g., CCD). Specifically, when a particular record is selected, as indicated by process block 42, the PHR program 16 checks to see whether the data when originally uploaded was associated with an XML stylesheet. Normally there will be no XML stylesheet for patient-entered data (A) and often there will be no XML stylesheet associated with data obtained from institutions (B)-(C) intending the data primarily for uploading to another institution's electronic medical record system. In these cases, an appropriate XML stylesheet 44 is generated (or selected from a library) as indicated by arrow 46 (and process block 43) to be included in files to be downloaded. Alternatively, any existing XML stylesheet may be replaced with a new stylesheet 44 providing a look and feel to the data consistent with the PHR website 10.

Figure 3:
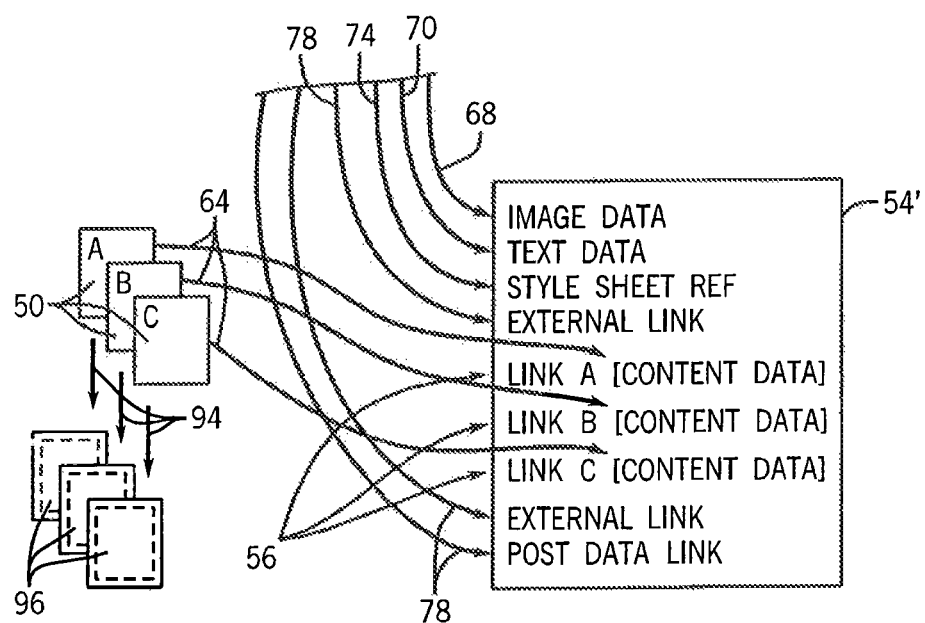
FIG. 3 is a data flow diagram similar to that of FIG. 2A showing augmentation of the index file and added downloaded files for enhanced remote user accessibility per the present invention.

Referring now to FIGS. 3 and 4, as indicated by process block 62, the PHR program 16 reviews the contents of the medical data files 50 and, as indicated by arrows 64, renames the links 56 in the index file 54' using specific content data so as to provide the user with a better understanding of the type of data associated with each of the medical data files 50. For example, the data source 40 for the medical data files 50, the type of document (e.g., a CCD document) deducible from the document header or selected by the PHR program 16, and the time range of the data of the medical data files 50 may be extracted from the medical data files 50 and used to label the links 56 as indicated by process block 63.

Figure 5:
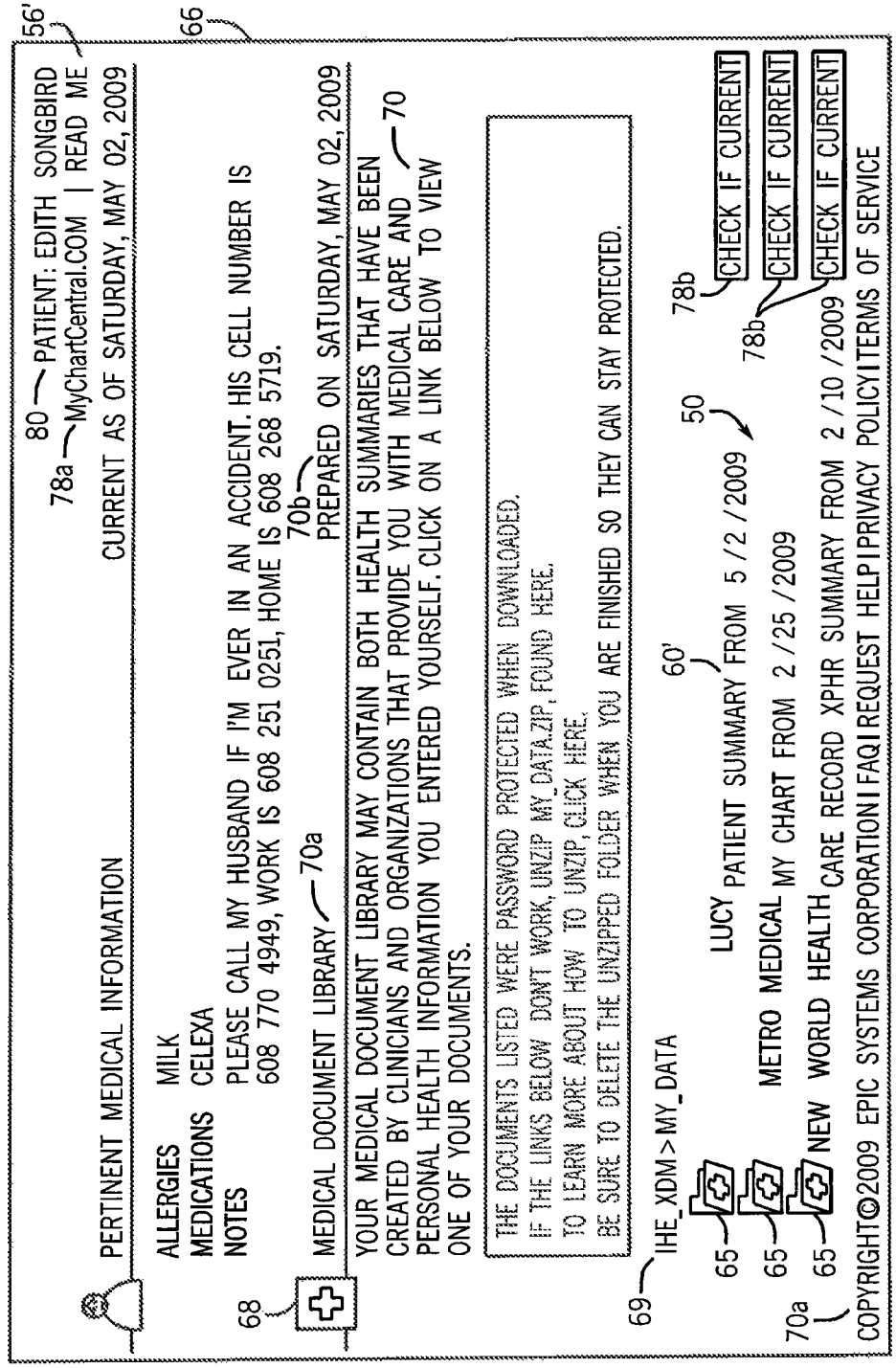
FIG. 5 is an example index file augmented per the present invention as displayed on a standard browser.

Specifically, referring to FIG. 5, an augmented index file 54' may be displayed on a browser to produce display 66 presenting augmented filename 60' now indicating the type of document (i.e., "Continuity of Care Document") and a Date Range (i.e., "Feb. 26, 2009") providing information about the medical data files 50 of greater assistance to the patient than a machine generated title. In addition, the data source 40 of the data of the medical data files 50 may be used to provide a heading 65 grouping medical data files 50 deriving data from similar sources. In this way, the index file 54 may be augmented to provide greater information about the particular medical data files 50 in an automatic fashion. The actual filename 69 of the data on the media 23 may also be provided but given a lesser prominence based on its reduced value to the patient.

Other files mandated by the standards but of lesser interest to the user may be indexed in a less prominent location and with smaller font, for example the "README" file 104 referenced by link 56'. The README file in the IHE standard provides data source information, and this data is incorporated into the index (as just described) reducing the relevance of this file to the patient while providing a more straightforward presentation of the data.

As shown in FIGS. 3 and 5, the index file 54 may be further augmented by the introduction of image data 68, ideally reflecting the same visual themes experienced by the patient when using the PHR website 10, thereby providing a consistent and familiar contextual environment for the data. Text 70 may be added explaining to the patient the purpose of the index and the scope of the indexed data of the medical data files 50. The text 70 may also include headings and standard legends 70a, as well as context information generated during the creation of the medical data files 50, for example the date of file creation and the name of the patient 70b, completing the patient experience and reinforcing the patient's understanding of the data. A stylesheet reference 74 associated and stored with the downloaded documents and referenced by the index file 54 may be used to further provide this consistent look and feel of the index file 54.

Importantly, the augmentation of the index file 54 may provide for one or more external links 78a to the patient's PHR allowing the patient to review the downloaded data while still having access to the other resources of the PHR website when an Internet connection is available. In this regard, the patient's login name may be embedded into the index document and optionally accessible by clicking on a patient full name 80 as shown in FIG. 5. When the link 78 to the PHR website is invoked, this patient's login name 80 may be posted to the web site during the linking to provide an expedited connection to the patient's PHR records where the login name is pre-populated and the patient needs only to enter a password.

This ability to communicate with the PHR website using downloaded context further permits a link 78b to be created allowing the patient to easily check if the data represented by the medical data files 50 is current, or the degree to which the medical data files 50 are not current. By posting the date of the download, or a "fingerprint" of the file data, such as a hash, the PHR website may respond with a web page indicating whether the data is essentially current or not, or optionally whether important changes have been made to the data. This may be permitted, with some limitations, by any possessor of the medical data files 50, even those without permission to access the patient data 14 through the PHR website 10. Such a feature might be usable in an emergency situation, for example.

Referring again to FIGS. 3 and 4, once the augmented data files have been created per process block 63, the patient may be prompted to indicate whether the files should be password-protected at process block 90. Such password protection may not be normally implemented by the electronic medical file standards, but may be desired, for example, if the files are not being transferred immediately to another health care institution and are being used by the patient for an on-person medical record, for example if he or she is traveling or the like, as is made practical by the present invention. Password protection preserves the security of the documents, if, for example, the thumb drive holding the files is lost.

If password protection is desired, then a password is input by the patient at process block 91 and, as indicated by arrows 94 of FIG. 3, the files 50 are converted to password-protected files 96. Such password-protected files may, for example, be in the form of PDF files, readable by most browsers, but further limiting the ability of the files to be accidentally modified.

Referring now to FIGS. 2 and 4, at process block 100 the augmented and generated files, including the medical data files 50, the index file 54, an XML stylesheet 44, an index HTML stylesheet 102, and other mandated files 104 such as the README file 104, may be packaged and zipped to produce a downloadable file 110. This file may then be downloaded per conventional techniques as indicated by process block 112.

Figure 6:
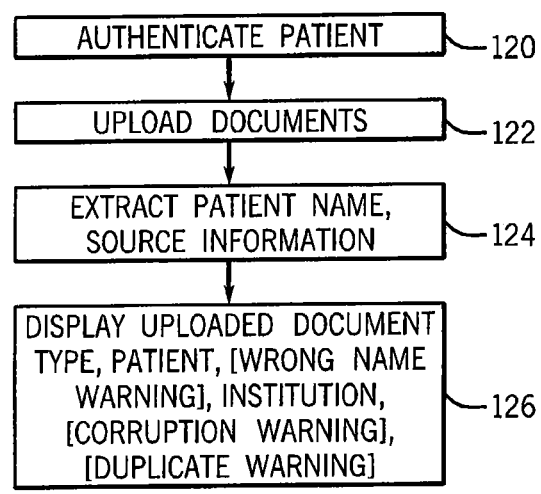
FIG. 6 is a flow chart showing enhancement of the uploading process by the PHR server computer of FIG. 1.

Referring now to FIG. 6, the above features of reading the medical data files to improve their accessibility suggests a similar technique for improving the uploading process for the patient when documents (such as CCD-compliant documents) are uploaded to the PHR website 10. As indicated by process block 120 and as executed by the computer 12 running PHR program 16, after authentication of the identity of a patient visiting the PHR website 10, a document to be uploaded may be identified as indicated by process block 122, for example, on a thumb drive or optical disk read by the computer 24 shown in FIG. 1.

The uploaded files may be placed in a temporary storage location on the computer 12 and, as indicated by process block 124, be interrogated to extract the patient name record 34 and the data source 40 fields from the files 50. At process block 126, each of the files together with extracted identifying information, including the patient name and the source institution name, may then be presented to the patient for confirmation that the correct files were uploaded. In this confirmation process the patient can view the name of the patient of the uploaded files to confirm that this is in fact the file he or she wishes to upload, this confirmation optionally being expressed as a warning if the patient identification used in the authentication of process block 120 differs from the patient name extracted from the files 50.

If the files are corrupted, as indicated by one or more error correction data blocks in the files, a corruption warning may be displayed. Further, the files may be reviewed to see if they are identical to previously uploaded files. Both of these situations can provoke a warning requiring an intentional patient override if uploading is to proceed.

Figure 7:
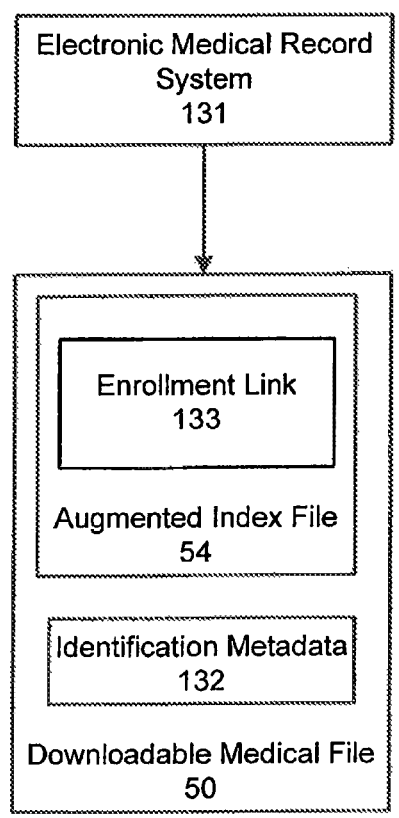
FIG. 7 is an electronic medical record system configured to generate a downloadable medical data file including encrypted metadata providing patient authentication.

Referring now to FIG. 7, a system 130 includes an electronic medical record system 131 configured to generate a downloadable medical data file 50 including encrypted metadata providing patient authentication 132 that will grant the patient improved access to an uploading process for the patient when documents (such as CCD-compliant documents) are uploaded to a second PHR website 10 is shown. The downloadable medical data files 50 may be generated by a healthcare provider facility that has provided care to the patient and maintained an electronic medical record for that patient. The downloadable medical files may be created and stored on a removable storage device 28.

Metadata 132 is data that describes other data stored in the downloadable medical files 50 may provide the functionality needed to manage and access the data in medical files 50. The metadata may be protected from manipulation and/or access using one or more methods of encryption. Exemplary encryption methods may include, but are not limited to, secret key encryption, public key encryption, symmetric key encryption, etc. According to an alternative embodiment, the metadata may be protected using a method and/or system other than encryption. According to yet another embodiment, the data may be unsecured such that it may be easily viewable and modifiable by the holder of the medical files 50.

Metadata 132 may be configured to include patient authentication information. The patient authentication information may be configured to include all of the information required for registration and access to the personal health record web site 10. The patient authentication information may further include all of the information required to allow the PHR web site 10 to access the original electronic medical record at the healthcare provider that originated the downloadable medical file 50 to allow the patient to later confirm, update, upload, etc. the data in the PHR website 10 with the data of the electronic medical record system 131.

According to one exemplary embodiment, metadata 132 may be provided as a part of an HTML file associated with a XDM downloaded record from a PHR portal system that allows the reader to check to see if the health information it contains is current and correct. The HTML file may be configured to include hyperlinks to each document contained in the XDM downloaded record. In this embodiment, the system that creates the HTML file may also writes into the HTML file a second hyperlink (one for each document) that points to the PHR portal system that created the file and takes the format https://www.PHRwebsite/CheckCurrency.aspx?CheckDocument=$documentID$hash, where $documentID is a unique identifier generated by the system that created the document and that can be used to point to additional information about when the document was created and under what circumstances, and the $hash is a cryptographic hash of the document included in the downloaded package. When the CheckCurrency webpage is accessed using system 10, it can communicate with the underlying EHR system associated with the PHR portal system to check the currency of the document.

The currency of the document may be checked in two ways. In one variant of the invention, the PHR portal system can use the document's unique ID to find the patient for whom the document was generated. The PHR portal system can then regenerate the document using the same algorithm by which the document was originally generated, recalculate the hash, and compare the resulting value with the original hash. If the hash is different, the data contained therein has changed. In a second variant of the invention, the PHR portal system can use the document's unique ID to find the patient for whom the document was generated and the date on which the document was generated. The PHR portal system can then use that date to determine if further activity has occurred in the patient's medical record after the point at which the document was generated, either through unambiguous cues, such as the record of an allergy which was created and associated with the patient after the time in question, or by less concrete events, such as a doctor's visit that occurred after that time.

Regardless of the check used, if the PHR portal system determines that information contained in the document on the portable media is not current, it can display a page to that effect to the viewer. In a further enhancement to this invention, it can display an authentication mechanism to the PHR website system 10 that will allow the user to enter his information, and, once authenticated, gain access to the most recent data.

Downloadable medical files 50 may be configured as described herein to allow a patient to browse and access the health records 34 stored therein using the style sheets to present a consistent look and feel. The downloadable medical files 50 may further be configured to provide a link configured to allow a user to automatically enroll and create an account on the PHR website 10 that will include the downloadable medical files 50 information. For example, the augmented index file 54' may be configured to include a button labeled "Enroll in PHR," including an enrollment link 133 that will initiate an enrollment process as further described below with reference to FIG. 8.

Figure 8:
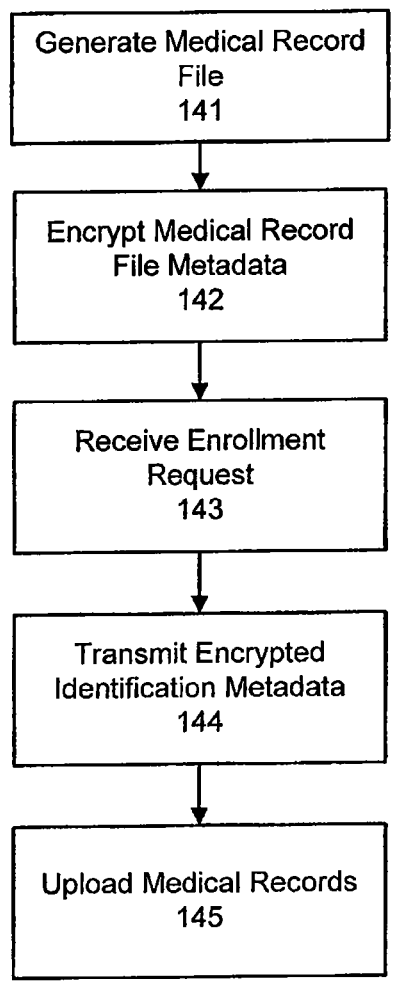
FIG. 8 is a flow chart showing an enrollment method for secured heath record account registration to a PHR server computer of FIG. 1.

Referring now to FIG. 8, an enrollment method 140 for secured health record account registration for improving the uploading process for the patient when documents (such as CCD-compliant documents) are uploaded to the PHR website 10 is shown. Improving the uploading process may include reducing registration overhead for the patient, increasing the validation level of the uploaded data, etc. The uploading process may be improved by including encrypted patient authentication metadata in downloadable medical files 50 generated by a healthcare provider.

In a step 141, an electronic medical record system 131 may receive a request to generate a downloadable medical record file 50. The file 50 may be generated by system 131 in accordance with XDM standards as known in the art and described herein. Generation of the file 50 may include the generation of metadata configured to allow for patient authentication. Patient authentication information may, according to an exemplary embodiment, be specifically configured to facilitate account creation and enrollment in a PHR website 10. Generation of the file 50 may also include generation of a PHR website enrollment link 133, for example as described above with reference to FIG. 7, to allow the patient to initiate an enrollment process.

In a step 142, the metadata may be encrypted and included in the downloadable medical file 50 in such a way as to prevent any viewing and/or modification of the underlying data. The majority of the information in the medical file 50 may remain unencrypted allowing the patient the option to browse and access the information as described herein.

In a step 143, the user may select the enrollment link 133 to initiate the process of enrolling with the PHR web site 10. Generally, this step may be performed by the use of his personal computing device 24. According to an exemplary embodiment, enrollment link 133 may be configured to initiate an automated enrollment process on the PHR website 10 by transmitting instructions contained entirely within the medical files 50 without requiring specialty programs or functions to be performed by the personal computing device 24.

The enrollment process may be implemented using an HTML file associated with a XDM downloaded record from a PHR portal system that allows a user to create an authenticated account at an unconnected PHR, such as system 10. The HTML file may be generated upon download by the PHR portal system and contains a hyperlink that points to a URL of this format: https://www.unconnectedPHR.com/NewAccount.aspx?loginInfo=$token$hash, where $token is a randomly generated guid and $hash is a non-reversible hash of the user's username and password at the PHR portal system along with a shared secret key between the portal 10 and the PHR system using the token as the nonce, a single use seed value. The $token$hash string may further be base64-encoded.

Upon clicking the hyperlink, the user may be presented with a webpage from portal 10 that requires entry of the username and password from the PHR portal system. The user re-enters his username and password, and the PHR system 10 checks the hash of those values and the prearranged shared secret key against the non-reversible hash in the query string, hashed again with the randomly generated token to validate the user's identity.

If the hash matches, PHR system 10 is able to determine that the user who has clicked the hyperlink is the same user who has downloaded the record. Further, the PHR system 10 is able to determine that the user's identity has been verified by the healthcare organization at which the user has an electronic health record based on possession of the password. These two factors may be configured to be prerequisites to the creation of a health record at the PHR system 10, to reduce the likelihood that the user in question is a fake user, a user posing as someone else, a spambot, etc. This assurance is provided without real-time communication between a PHR portal system and PHR system 10 and does not require creating a secured connection between the PHR portal system and PHR system 10 or further business arrangements that might be required by law for a more tightly integrated connection.

After the user is verified and finishes creating an account with the PHR system 10, system 10 is prompted to upload the document(s) referenced by the HTML file, thereby keeping them in a permanent storage that is more secure and more accessible than optical flash media. The user is automatically prompted to take this step upon account verification by virtue of the unconnected PHR flagging his pending account with a specific flag that indicates it was created from a hyperlink in a downloaded record. In a step 145, the PHR website system 10 may be configured to upload the downloadable medical files 50 for inclusion in the automatically generated user account based on the identification information. The identification information may be stored by PHR web site 10 for future updating directly from the electronic medical record system 131, etc.

According to one exemplary embodiment, encrypted metadata may be configured by the portal system to contain a universal object identifier that specifies the healthcare organization that provided the downloaded record to the user. If the organization has already established a secure connection and appropriate business relationship with the PHR system 10, such an identifier could prompt the user, once his user account at the PHR system 10 is created, to establish a secure and persistent link to that organization. This link would provide a more convenient way to obtain a permanent and portable copy of the information previously contained in the downloaded file. If the organization from which the user downloaded his record has not established a secure connection and appropriate business relationship with the PHR system 10 but chooses to do so in the future, the PHR system 10 could at that point prompt the user to establish the secure and persistent link.

According to another exemplary embodiment, the encrypted metadata may be configured by the portal system to contain demographic information about the user who downloaded the record from the PHR portal system. This demographic information could be used as part of the user's new account, either to save the user the time of typing the information himself, or as information that is verified as correct by the organization that created the downloaded record and thus that cannot be changed by the patient. If the user has an account at the PHR system 10 that is not known to the organization that created the download, this extra demographic data could be used to run a deterministic search on the databases of PHR system 10 to find that account and thereby prevent the user from creating a duplicate.

According to another exemplary embodiment, the PHR portal system and PHR system 10 both have knowledge in their databases if a paired (linked) user record exists in both their systems and corresponds to a single human being, through the exchange of user identifier tokens. If the PHR portal system that generates the HTML file receives information from PHR system 10 indicating that the user to already has an account in the PHR system 10, the PHR portal system may be configured to, instead of providing an enrollment hyperlink, instead provide a hyperlink that prompts the user to re-enter his password information for the PHR system 10 and, upon doing so, logs him into the PHR system 10. Since the hyperlink would provide the shared identifier token to the PHR system 10, PHR system 10 no longer needs to prompt the user for his username. The information is embedded in the user's record that is identified by the identifier token in the hyperlink.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A computer-implemented system for implementing an improved personal health record enrollment process, comprising:
   an electronic medical record system configured to generate an index file, the index file including a plurality of links to individual records of patient medical data including the clinical records of the patient, wherein the index file is augmented with encrypted metadata generated based on the patient medical data and configured to include a non-reversible hash of the patient authentication information along with a prearranged secret key shared between the electronic medical record system and a personal health record system; and
   the personal health record system configured to implement a patient enrollment process including the steps of:
   a) receiving patient authentication input;
   b) authenticating the patient authentication input based on the received patient authentication information in the encrypted metadata in the index file by checking the hash of the patient authentication input and the prearranged shared secret key against the non-reversible hash in the encrypted metadata, hashed again with a randomly generated token to validate the user's identity, and c) generating a patient enrollment account for the patient based at least in part on the authentication.

2. The system of claim 1, wherein the patient enrollment process further includes the step of receiving the patient medical data for storage and association with the patient enrollment account.

3. The system of claim 1, wherein the index file includes a link to the personal health record web portal, the link including initiating the enrollment process.

4. The system of claim 1, wherein the personal health record system is configured to establish whether more current patient medical data is present at the electronic medical record system using the patient authentication information received from the encrypted metadata.

5. The system of claim 1, wherein the an electronic medical record system is further configured to generate a generic HTML stylesheet allowing the patient medical data to be displayed in a user-viewable format.

6. The system of claim 5, wherein displaying the patient medical data in a user-viewable format includes providing an enrollment button associated with a link to initiate the patient enrollment process.

7. The system of claim 1, wherein the personal health record system is configured to search a personal health record database using the patient authentication information to identify an existing patient enrollment account having the same patient authentication.

8. The system of claim 7, further including storing the patient medical data in the existing patient enrollment account.

9. A computer-implemented system for implementing an improved personal health record enrollment process, comprising:

a personal health record system configured to implement a patient enrollment process including the steps of:
a) receiving portable storage medium at an input device of the personal health record system, the medium including patient medical data and encrypted metadata associated with the patient medical data, the encrypted medical data including a non-reversible hash of patient authentication information along with a prearranged secret key shared between the electronic medical record system and a personal health record system;
b) receiving patient authentication input at an input device of the personal health record system provided by a user;
c) authenticating the patient authentication input from the user based on the received patient authentication information in the encrypted metadata in the index file by checking the hash of the patient authentication input and the prearranged shared secret key against the non-reversible hash in the encrypted metadata, hashed again with a randomly generated token to validate the user's identity, and
d) generating a patient enrollment account for the patient based at least in part on the authentication.

10. The system of claim 9, wherein the patient enrollment process further includes the step of receiving the patient medical data for storage and association with the patient enrollment account.

11. The system of claim 9, wherein the encrypted metadata is incorporated within a link to the personal health record system, the link including initiating the enrollment process.

12. The system of claim 9, wherein the personal health record system is further configured to establish whether more current patient medical data is present at an electronic medical record system that generated the patient medical data using the authentication information received from the encrypted metadata.

13. The system of claim 9, wherein the portable storage medium further includes a generic HTML stylesheet allowing the patient medical data to be displayed in a user viewable format.

14. The system of claim 13, wherein displaying the patient medical data in a user viewable format includes providing an enrollment button associated with a link to initiate the patient enrollment process.

15. The system of claim 9, wherein the personal health record web portal is configured to search a personal health record database using the patient authentication information to identify an existing patient enrollment account having the same patient authentication information.

16. The system of claim 15, further including storing the patient medical data in the existing patient enrollment account.

17. A computer-implemented method for implementing an improved personal health record enrollment process, comprising:

generating an index file in a format viewable in a browser interpreting HTML, the index file including encrypted metadata based on patient medical data and configured to include a non-reversible hash of patient authentication information along with a prearranged secret key shared between the electronic medical record system and a personal health record system;
storing the patient the index file in association with the patient medical data on a portable data storage device;
receiving patient authentication input, encrypting the patient authentication information, and comparing the encrypted patient authentication input to the encrypted metadata by checking a hash of the patient authentication input and the prearranged shared secret key against the non-reversible hash encrypted in the encrypted metadata, hashed again with a randomly generated token to validate the user's identity;
displaying the patient medical data based on the index file based on a successful comparison, including displaying a enrollment link to initiate a patient enrollment process;
transmitting the encrypted metadata including the patient authentication information upon selection of the enrollment link to initiate generation of a patient enrollment account based on the patient authentication information; and
uploading the patient medical data for storage and association with the patient enrollment account.

18. The method of claim 17, further including determining whether more current patient medical data is present at the electronic medical record system using the identification information received from the encrypted metadata.

19. The method of claim 17, wherein the index file further includes a generic HTML stylesheet allowing the patient medical data to be displayed in a user viewable format.

20. The method of claim 19, wherein displaying the patient medical data includes displaying the data in a user viewable format based on the generic HTML stylesheet and providing an enrollment button associated with a link to initiate the patient enrollment process.

21. The method of claim 17, further including searching a personal health record database using the patient authentication information to identify an existing patient enrollment account having the same patient authentication information.

22. The method of claim 21, further including storing the patient medical data in the existing patient enrollment account.

* * * * *